United States Patent
Okamoto (10) Patent No.: US 9,636,001 B2
(45) Date of Patent: May 2, 2017

(54) INTRODUCTION DEVICE (71) Applicant: OLYMPUS CORPORATION, Tokyo (JP)

(72) Inventor: Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 170 days.

(21) Appl. No.: 14/613,517

(22) Filed: Feb. 4, 2015

(65) Prior Publication Data

US 2015/0208902 A1 Jul. 30, 2015

Related U.S. Application Data (63) Continuation of application No. PCT/JP2014/063445, filed on May 21, 2014.

(30) Foreign Application Priority Data

Jun. 20, 2013 (JP) ................. 2013-129853

(51) Int. Cl.
- *A61B 1/00* (2006.01)
- *A61B 1/005* (2006.01)
- *G02B 23/24* (2006.01)
- *G05G 5/05* (2006.01)

(52) U.S. Cl.
CPC ........ *A61B 1/0052* (2013.01); *G02B 23/2476* (2013.01); *G05G 5/05* (2013.01); *A61B 1/0016* (2013.01); *Y10T 74/2042* (2015.01)

(58) Field of Classification Search
CPC ............................ A61B 1/0052; A61B 1/0057
USPC .................................................. 600/146–150
See application file for complete search history.

(56) References Cited

U.S. PATENT DOCUMENTS 4,499,895 A * 2/1985 Takayama ............ A61B 1/0052 388/838
2006/0089535 A1 4/2006 Raz et al.
2013/0102960 A1 4/2013 Miyoshi

FOREIGN PATENT DOCUMENTS

| JP | H06-277176 A | 10/1994 |
| JP | 2009-219822 A | 10/2009 |
| JP | 5210465 B2 | 3/2013 |
| WO | WO 2012/074013 A1 | 6/2012 |
| WO | WO 2012/132636 A1 | 10/2012 |
| WO | WO 2012/172953 A1 | 12/2012 |

OTHER PUBLICATIONS

English version of the International Search Report dated Jun. 24, 2014 from related International Application No. PCT/JP2014/063445.

(Continued)

*Primary Examiner* — Matthew J Kasztejna
(74) *Attorney, Agent, or Firm* — Scully, Scott, Murphy & Presser, P.C.

(57) ABSTRACT

An introduction device applies urging force linearly generated by a spring to a nut portion screwed to a drive shaft to convert the urging force to the rotation direction of the drive shaft. This conversion returns an RL operation dial provided at the end of the drive shaft in a direction opposite to the rotation direction in which the RL operation dial is operated, and then returns the RL operation dial to an original neutral position.

6 Claims, 7 Drawing Sheets

(56) References Cited

OTHER PUBLICATIONS

English translation of International Preliminary Report on Patentability dated Dec. 30, 2015 together with the Written Opinion received in related International Application No. PCT/JP2014/063445.
Extended Supplementary European Search Report dated Feb. 17, 2017 in related European Patent Application No. 14 81 3292.1.

* cited by examiner

INTRODUCTION DEVICE

CROSS-REFERENCE TO RELATED APPLICATIONS

This is a Continuation Application of PCT Application No. PCT/JP2014/063445, filed May 21, 2014, which was published under PCT Article 21(2) in Japanese. This application is based upon and claims the benefit of priority from prior the Japanese Patent Application No. 2013-129853, filed Jun. 20, 2013, the entire contents of which are incorporated herein by references.

BACKGROUND OF THE INVENTION

1. Field of the Invention

The present invention relates to an introduction device comprising an operation input unit which returns into a range including a predetermined neutral position when a hand is taken off in the middle of operation.

2. Description of the Related Art

As an introduction device, a medical or industrial endoscopic device to insert an elongate and flexible insertion portion which is provided with a curving portion at the distal end has been typically utilized for visual observation in a body cavity or in a conduit having curved parts. For example, when the medical endoscopic device is used for a diagnosis or surgery in the body cavity, the inside of the body cavity is observed while an operation portion comprising two operation dials is operated to curve the curving portion provided on the distal side of the insertion portion in an up-down (UD) direction and a right-left (RL) direction.

If the curving portion is electrically operated, the degree of curving the curving portion relative to the rotation angles of the operation dials can be freely set. That is, if a lower ratio of the curving angle at which the curving portion is curved to the rotation angles of the operation dials is set, it will be easier for an operator to more finely and slowly curve the curving portion. If the operation dials are configured to perform multi-rotation operation for one or more rotations (360 degrees or more) so that the curving portion can curve more slowly and finely, the operator operates the curving portion while repeatedly rotating the operation dials clockwise and counterclockwise. In this instance, it is difficult for the operator to recognize the curving state of the curving portion from the current rotational positions of the operation dials. For example, in the case of an operation dial capable of one and a half rotations (450 degrees), it may be difficult to recognize whether the current rotational position is 60 degrees or 420 degrees. When the operator cannot recognize the angle, the operator once stops the observation, returns the operation dials to a neutral position (e.g. scale 0) while looking at the operation dials at hand, and then again performs the curving operation.

For example, Jpn. Pat. Appln. KOKAI Publication No. 2009-219822 has suggested an endoscopic device which curves a curving potion by driving a motor. The curving potion of this endoscopic device is provided with a neutral return mechanism in which two spiral springs that are wound in opposite directions with respect to the rotation axis of an operation dial are arranged to face each other to return the operation dial to a neutral position. This neutral return mechanism is adjusted so that when the operation dial is rotated, one of the spiral springs is compressed, and the other spiral spring is expanded, and urging force thereby works to return the operation dial to the initial position (neutral position) where the curving potion linearly extends.

In an endoscopic device suggested in International Publication No. WO2012/074013A1, an RL operation dial to electrically curve a curving potion in the RL direction is disposed under an operation portion. It is shown that this RL operation dial is rotated by, for example, the second finger of a hand grasping the operation portion.

BRIEF SUMMARY OF THE INVENTION

According to an embodiment of the present invention, there is provided an introduction device comprising: a curvable curving potion; a rotor which is rotated by an operator and which curves the curving potion; a shaft rotatable around the rotation axis of the rotor in response to the rotation of the rotor; an elastic body which is elastically deformed in response to the rotation of the shaft and which generates urging force to return the rotor; a shaft rotor which deforms the elastic body in the rotation axis direction to generate the urging force of the elastic body in the rotation axis direction; and a screw shaft which is formed as a screw in the shaft and which screws in the shaft rotor and which moves the shaft rotor in the rotation axis direction.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE PREFERRED EMBODIMENT

Hereinafter, embodiments of the present invention will be described in detail with reference to the drawings.

First Embodiment

Figure 1:
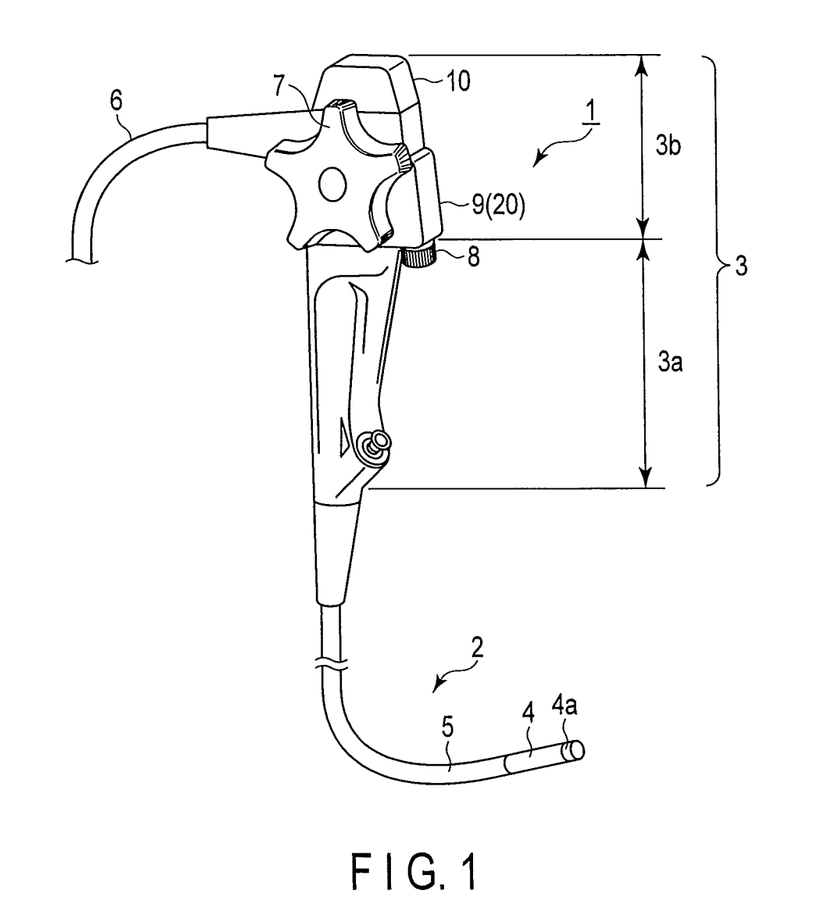
FIG. 1 is a diagram showing the exterior configuration of an endoscopic body according to a first embodiment.

FIG. 1 is a diagram showing the exterior configuration of an endoscopic body according to a first embodiment.

In the example described according to the present embodiment, an introduction device 1 is applied to a medical endoscopic device intended for observation in a lumen or a body cavity of a living body, or an industrial endoscopic device for observation in a pipe or an engine.

The introduction device 1, that is, the endoscopic device roughly has an insertion portion 2 to be inserted into the body cavity from the distal side, an operation portion 3 coupled to the proximal side of the insertion portion 2, and a universal cord 6 including a light guide and a signal cable extending from the operation portion 3.

The insertion portion 2 comprises a flexible tube 5 which curves flexibly, a curving potion 4 which is curved in up-down (UD) and right-left (RL) directions relative to an insertion direction, and a distal portion 4a which is provided at the distal end of the curving potion 4 and which is provided with an observation window, an illumination window, and a forceps hole that are not shown.

The operation portion 3 comprises a grip portion 3a connected to the insertion portion 2, a UD knob (rotation knob) 7 which curves the curving potion 4 in the up-down (UD) direction, a right-left (RL) operation dial 8 for curving the curving potion 4 in the RL direction, an operation portion body 3b in which a later-described input unit 20 including the RL operation dial 8 is disposed, and an electric curving drive mechanism 10 including a motor (not shown) to serve as an electric driving source housed in the upper part of the operation portion 3.

The curving potion 4 is disposed on the distal side of the insertion portion 2, and stages of the curving potion 4 are joined in a longitudinal direction so that metallic joint rings sequentially range to stagger 90 degrees in a diametrical direction. Between the joint rings, two joints are formed at opposite positions, and are substantially coaxially joined rotatably relative to each other to constitute a curving mechanism. Normally, the curving mechanism is watertightly covered with a flexible sheet-like material. At least two angle wires are coupled to each of the joint rings of the curving mechanism, and when each of the angle wires is pulled, a curving operation is performed to achieve bending between the joints. The electric curving drive mechanism 10 performs a curving operation in the RL direction between the joints by pulling the angle wires using an actuator such as a motor. The degree of pulling is adjusted to a desired curving angle by the operation amount of the RL operation dial 8. The curving potion 4 and the electric curving drive mechanism 10 constitute a curving function portion.

The grip portion 3a is provided with an insertion hole (forceps hole) to insert a forceps or a surgical instrument. As will be described later, one part of the input unit 20 is disposed in a hollow protrusion 9 which is formed so that the RL operation dial 8 is exposed and protrude out of the housing of the operation portion 3, and the other part of the input unit 20 is disposed outside the housing. In the present embodiment including embodiments and modifications described below, the RL operation dial 8 (rotor) is a multi-rotation element capable of one or more rotations (360 degrees or more).

In the shape example of the operation portion 3 according to the present embodiment, the housing in which operational components are disposed is rectangular, and the tapered grip portion 3a is integrally attached to the bottom of the housing. The flexible tube 5 of the insertion portion is provided to extend from the lower distal end of the grip portion 3a.

In the operation portion 3 described below, a surface (UD knob disposing surface) in which the UD knob 7 is disposed rotatably around a rotation axis extending in a direction that intersects with the longitudinal axis of the grip portion at a position operable by the thumb of the hand grasping the grip portion 3a in the operation portion body 3b is a front surface, and a surface on which the palm of the hand abuts on the opposite side is a rear surface. A surface which follows the front surface and rear surface of the operation portion 3 and which extends in a direction along the rotation axis of the UD knob and in which the universal cord 6 extends is a first side surface. A surface which is located on the side opposite to the first side surface across the longitudinal axis of the grip and which extends along the rotation axis of the UD knob and in which the RL operation dial 8 is disposed is a second side surface. A surface of the grip portion 3a to which the proximal end of the insertion portion 2 is attached is the bottom surface (or proximal side) of the operation portion. The side (the electric curving drive mechanism 10) opposite to the bottom surface of the operation portion 3 is an upper surface or an upper part. In the present embodiment, the above-mentioned motor and others are housed in the upper side of the operation portion 3.

In the present embodiment, the fingers of the hand grasping the operation portion 3 are generally arranged (not shown) so that the thumb turns to the front surface from the first side surface and is caught on the protrusion of the star-shaped UD knob 7. The first finger which has turned around the rear surface reaches the second side surface to be able to operate an unshown switch such as a water supply button. Moreover, the second finger is located to be caught on the protrusion of the UD knob 7 on the side opposite to the thumb. The third finger has its tip caught on the RL operation dial 8 from the lower side of the above-mentioned protrusion 9 of the operation portion 3 and is able to rotate the RL operation dial 8. The little finger is caught on the grip portion 3a, and holds so that the operation portion 3 is stably grasped.

Although not shown, it should be understood that a known system has, when the introduction device 1 is an endoscopic device, an image processor which performs image processing of an obtained video signal, a universal light source which generates illumination light, a controller (control unit) which controls the curving of the curving potion in accordance with an instruction from an imaging unit provided in the observation window or from an operational instruction unit provided in the operation portion and which controls the entirety including each driver, a motor driving electric power supply which supplies electric power to drive the electric curving drive mechanism 10, a monitor to display an image-processed observation image, and an input unit such as a keyboard for setting and selection.

Figure 2:
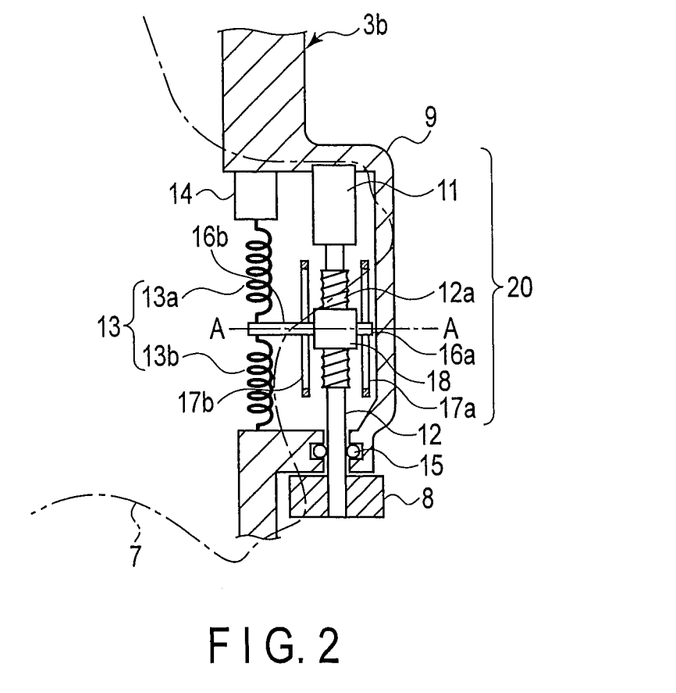
FIG. 2 is a diagram showing the layout configuration example of an input operation part and a neutral return mechanism in an input unit disposed in an operation portion.
Figure 3A:
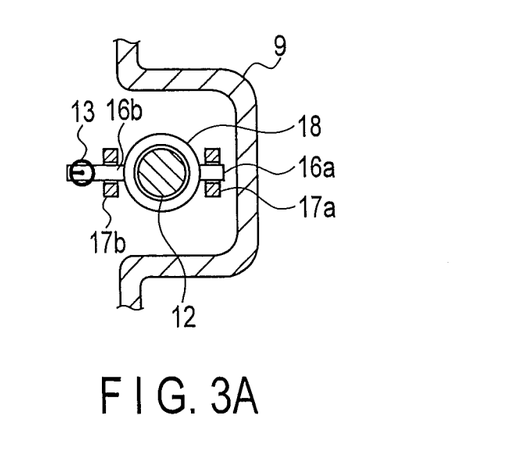
FIG. 3A is a diagram conceptually showing the sectional configuration of the input unit viewed from the plane A-A shown in FIG. 2.
Figure 3B:
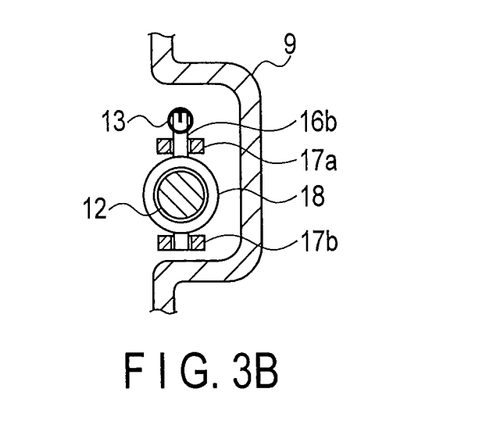
FIG. 3B is a diagram conceptually showing the sectional configuration of the input unit in which the arrangement direction of the input unit in FIG. 3A has changed.

FIG. 2 is a diagram showing the configuration example of an operator which is an input operation part and a neutral return mechanism in the input unit disposed in the operation portion according to the present embodiment. FIG. 3A is a diagram conceptually showing the sectional configuration of the input unit viewed from the plane A-A shown in FIG. 2. FIG. 3B is a diagram conceptually showing the sectional configuration of the input unit in which the arrangement direction of the input unit has changed.

Now, the input unit 20 according to the present embodiment is described. In the the present embodiment, an initial rotational position (e.g. scale 0) of the RL operation dial 8 of the input unit is a neutral position where the curving state of the curving potion 4 is a substantially linear neutral state.

The input unit 20 roughly comprises the operator and the neutral return mechanism. Specifically, the operator comprises the RL operation dial 8, a drive shaft (shaft) 12 erected on the RL operation dial 8, and a potentiometer 11 provided at the distal end of the drive shaft 12. Since the RL operation dial 8 is disposed to be exposed outside the operation portion 3, an O-ring 15 or the like is disposed in the part of the operation portion housing into which the drive shaft 12 is introduced to provide a watertight configuration that prevents liquid and foreign bodies from entering the operation portion housing from the outside.

The neutral return mechanism comprises a screw shaft 12a in which an external thread is formed in the middle of the drive shaft 12, a nut portion 18 (shaft rotor) which is movably threaded into the screw shaft 12a, guide shafts 16a and 16b extending from the side surface in the diametrical direction of the nut portion 18, guide portions 17a and 17b in which long holes are formed to fit and define the guide shafts 16a and 16b in the movement range of the nut portion 18, and elastic bodies such as tension springs (hereinafter referred to as springs) 13 attached at one end to the upper and lower surfaces at the ends of the guide shaft 16b longer than the guide shaft 16a. The screw shaft 12a and the nut portion 18 may have the configuration of what is known as a ball screw in which balls intervene.

These springs 13 (13a and 13b) have the same elastic characteristics. The other end of the spring 13a is fixed to a spring support portion 14. The other end of the spring 13b is directly fixed to the operation portion housing. The spring support portion 14 is used when the springs are characteristically different or used as an adjusting member to set a neutral position. Therefore, the spring support portion 14 is not essential, and the other end of the spring 13a may be directly fixed to the operation portion housing.

The guide portions 17a and 17b guide the guide shafts 16a and 16b in the long holes so that the guide shafts 16a and 16b do not rotate in the horizontal direction. Thus, if the drive shaft 12, that is, the screw shaft 12a rotates, the nut portion 18 moves up and down within the range of the long holes. In the present embodiment, the position of the nut portion 18 when urging forces (or regression force) resulting from the elasticity of the springs 13a and 13b are in proportion is the neutral position where the curving potion 4 is substantially linear.

FIG. 3A conceptually shows the sectional configuration of the input unit viewed from the plane A-A shown in FIG. 2. The drive shaft 12 and the potentiometer 11 are arranged in the protrusion 9 of the operation portion 3. The guide parts of the neutral return mechanism are arranged on both sides of the drive shaft 12. The springs (elastic members) 13 serving as a driving source of returning are located closer to the longitudinal axis of the grip portion than the drive shaft 12.

As a modification, in FIG. 3B, the whole input unit 20 is housed in the protrusion 9 of the operation portion 3. In contrast to FIG. 3A, a first unit comprising the guide shafts 16a and 16b and the springs 13a and 13b and constituting the neutral return mechanism has changed its direction in an orthogonal direction and is disposed in the protrusion 9 so that the first unit is parallel to the second side surface. That is, compared to the UD knob 7 which rotates around a rotation shaft protruding in the UD knob 7 disposing surface, the first unit and a second unit which comprises the screw shaft 12a, the nut portion 18, and the guide portions 17a and 17b are arranged in the protrusion 9 along the axial direction of the rotation axis of the UD knob 7. In this arrangement, the protruding width of the protrusion 9 is further reduced than in FIG. 3A, so that the width of the space between the first side surface and the second side surface of the operation portion 3 can be reduced, and the operability of the fingers improves.

In this configuration, if the operator rotates the RL operation dial 8 to curve the curving potion 4, the drive shaft 12 rotates, and the nut portion 18 to be threaded into the screw shaft 12a slides. At the same time, the rotation amount (rotation angle) of the drive shaft 12 is detected by the potentiometer 11. In accordance with the detected value (output signal value), the controller moves the electric curving drive mechanism 10 so that the curving potion 4 will have a predetermined curving angle.

In response to the sliding of the nut portion 18, one of the springs 13a and 13b fixed to the guide shaft 16b is compressed, and the other expands. As a result, one of the springs 13a and 13b generates urging force for expansion, and the other generates urging force for contraction. However, the urging force for contraction may not be generated depending on the shape of the spring.

Due to the urging forces, the nut portion 18 is drawn back to the original neutral position. In the present embodiment, the nut portion 18 is not necessarily configured to return to the original neutral position. That is, a stop position is provided with an allowance as a neutral return range by loosely spreading the springs 13a and 13b with slight tension or without tension when both ends of each of the springs 13a and 13b are fixed to the guide shaft 16b and the operation portion housing or the spring support portion 14 so that the nut portion 18 may stop in the vicinity of the neutral position. The O-ring 15 is fitted to the drive shaft 12, and may function as a braking element in rotation.

Therefore, if the nut portion 18 is within the neutral return range, the urging forces of the springs 13a and 13b do not work, the nut portion 18 is stopped at the current position even if the operator takes the hand off the RL operation dial 8. That is, this suggests that the curving state of the curving potion 4 is maintained even if the operator takes the hand off the RL operation dial 8. This range is properly set at the time of designing, and is not limited.

As described above, according to the present embodiment, the urging force linearly generated by the spring is applied to the nut portion screwed to the drive shaft 12 and thus converted in the rotation direction of the drive shaft 12. This conversion allows the RL operation dial provided at the end of the drive shaft 12 to return to the direction opposite to the rotation direction in which the RL operation dial has been operated and allows the RL operation dial to return to the original neutral position. Moreover, a neutral return mechanism reduced in size is obtained by the configuration in which the operator of the input unit 20 and the neutral return mechanism are biaxially provided in parallel. Further, the neutral return mechanism can be disposed inside the operation portion housing, and the input unit 20 is reduced in size. Thus, it is possible to obtain an endoscopic device, that is, an introduction device which inhibits the size increase of the operation portion resulting from electrification and which has the operation portion that is balanced in weight.

Second Embodiment

Figure 4:
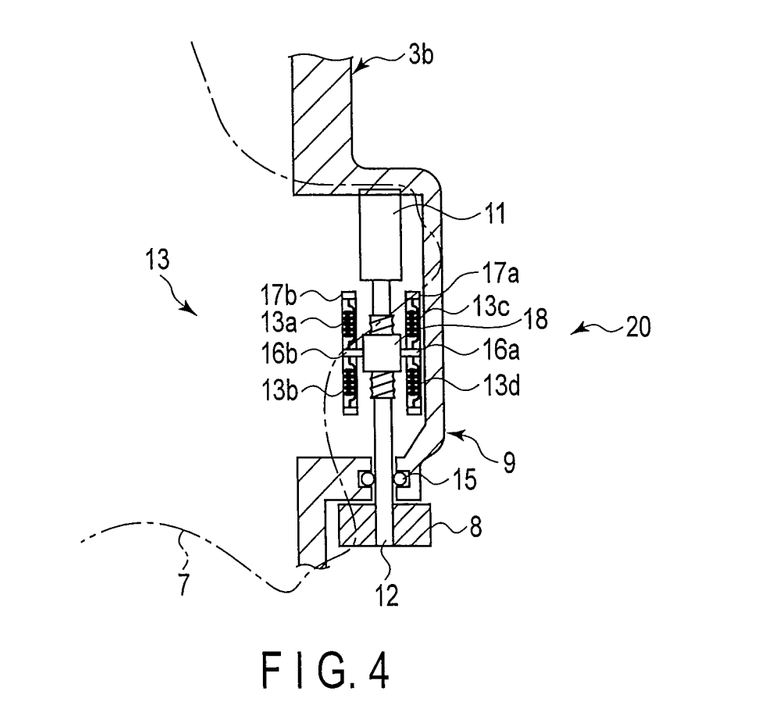
FIG. 4 is a diagram showing the conceptual configuration of an input unit housed in an operation portion according to a second embodiment.

FIG. 4 is a diagram showing the conceptual configuration of an input unit housed in an operation portion according to a second embodiment. Components in the present embodiment equivalent to those in the first embodiment described above are provided with the same reference signs, and are not described. Although not shown, an operation portion 3 according to the present embodiment includes the grip portion 3a and the operation portion body 3b that have been described above. The operation portion body 3b also has a UD knob (rotation knob) 7 and an RL operation dial 8.

An input unit 20 according to the present embodiment comprises an operator and a neutral return mechanism. The operator comprises the RL operation dial 8, a drive shaft 12, and a potentiometer 11. The neutral return mechanism comprises a screw shaft 12a, a nut portion 18, guide shafts 16a and 16b, guide portions 17a and 17b, and springs 13 (13a, 13b, 13c, and 13d) attached to long holes of the guide portions 17a and 17b. The space between the drive shaft 12 and an operation portion housing is watertightly configured by an O-ring 15. The screw shaft 12a and the nut portion 18 may have the configuration of the ball screw in which balls intervene.

In the configuration according to the present embodiment, the above-mentioned springs 13 (13a, 13b, 13c, and 13d) are fixed to the guide shafts 16a and 16b in the long holes of the guide portions 17a and 17b. Specifically, as shown in FIG. 4, the springs 13a and 13b are fixed at one end to both surfaces of the guide shaft 16a, and fixed at the other end to both ends of the long hole of the guide portion 17a. Similarly, the springs 13c and 13d are fixed at one end to both surfaces of the guide shaft 16b, and are fixed at the other end to both ends of the long hole of the guide portion 17b.

In this configuration, the RL operation dial 8 is rotated to curve a curving potion 4. The curving potion 4 is curved, and the nut portion 18 is moved in one direction on the screw shaft 12a.

Furthermore, when the operator takes the fingers off the RL operation dial 8, the nut portion 18 slides back into the neutral return range including a predetermined neutral position because of the urging force of the springs 13. The operational principle of the neutral return according to the second embodiment is only different from that in the first embodiment described above in the locations of the springs, and is equivalent to that in the first embodiment.

According to the present embodiment, it is possible to obtain advantageous effects equivalent to those in the first embodiment described above. Moreover, the springs 13 are configured to be disposed in the long hole of the guide portion 17a, which allows further reductions in size and weight. As the spring 13, a tension spring may be used as in the present embodiment, or a compression spring may be used.

Third Embodiment

Figure 5:
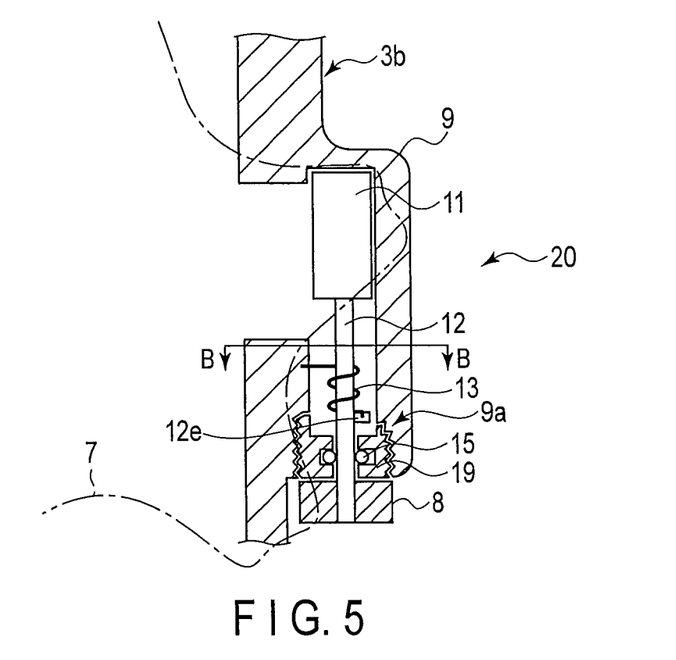
FIG. 5 is a diagram showing the conceptual configuration of an input unit housed in an operation portion according to a third embodiment.
Figure 6A:
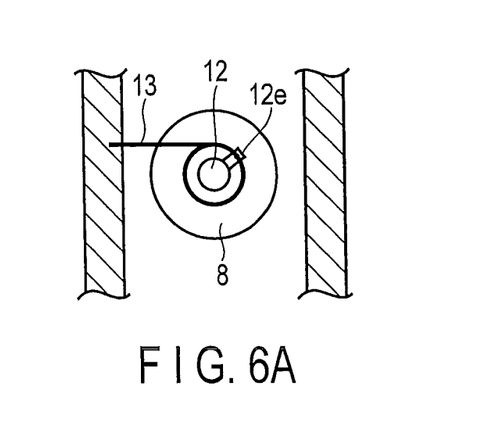
FIG. 6A is a diagram showing a spring fitted to a rotary dive shaft when viewed from the direction of B-B in FIG. 5.
Figure 6B:
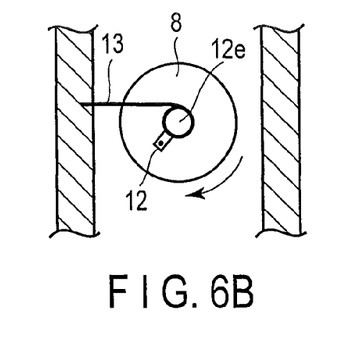
FIG. 6B is a diagram showing the spring fitted to the rotary dive shaft when viewed from the direction of B-B in FIG. 5.
Figure 6C:
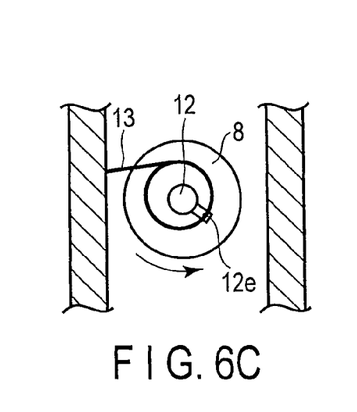
FIG. 6C is a diagram showing the spring fitted to the rotary dive shaft when viewed from the direction of B-B in FIG. 5.
Figure 6D:
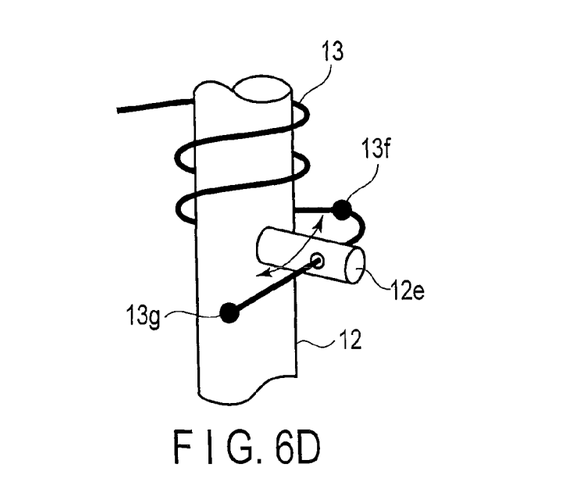
FIG. 6D is a diagram showing a configuration example for setting a neutral return range.

FIG. 5 is a diagram showing the conceptual configuration of an input unit housed in an operation portion according to a third embodiment. FIGS. 6A, 6B and 6C are diagrams showing a spring fitted to a rotary dive shaft when viewed from the direction of B-B in FIG. 5. FIG. 6D is a diagram showing a configuration example for setting a neutral return range. Components in the present embodiment equivalent to those in the first embodiment described above are provided with the same reference signs, and are not described. Although not shown, an operation portion 3 according to the present embodiment includes the grip portion 3a and the operation portion body 3b that have been described above. The operation portion body 3b also has a UD knob (rotation knob) 7 and an RL operation dial 8.

An input unit 20 according to the present embodiment comprises an operator and a neutral return mechanism. The operator comprises the RL operation dial 8, a drive shaft 12 erected on the RL operation dial 8, and a potentiometer 11 provided at the distal end of the drive shaft 12. The space between the drive shaft 12 and an operation portion housing is watertightly configured by an O-ring 15.

The neutral return mechanism comprises a spring fixing portion 12e provided in the middle of the drive shaft 12, and a spring (spiral coil spring) 13 fitted to the drive shaft 12. The spring 13 is fitted to the drive shaft 12, and has one end fixed to, for example, a rib of the operation portion housing and the other end fixed to the spring fixing portion 12e. In this configuration, FIG. 6A shows the state of the spring 13 when the RL operation dial 8 is at a neutral position. When the RL operation dial 8 is rotated clockwise, the coil diameter of the spring 13 decreases (decreases in diameter) so that the spring 13 winds around the drive shaft 12 as shown in FIG. 6B.

On the other hand, when the RL operation dial 8 is rotated counterclockwise, the coil diameter of the spring 13 increases (increases in diameter) so that the spring 13 further comes away from the drive shaft 12 as shown in FIG. 6C. In each case, when the coil diameter of the spring 13 changes, urging force works for a return to the original neutral position. That is, when the coil diameter of the spring 13 decreases, the RL operation dial 8 is returned in a direction (counterclockwise direction) opposite to an arrow direction shown in FIG. 6B and then rotated and moved to the vicinity of the neutral position. On the other hand, when the coil diameter of the spring 13 increases, the RL operation dial 8 is returned in a direction (clockwise direction) opposite to an arrow direction shown in FIG. 6C and then rotated and moved to the vicinity of the neutral position.

In the third embodiment, as a configuration example for setting the above-mentioned neutral return range, a through-hole having a diameter to allow the passage of the spring 13 is made in the spring fixing portion 12e as shown in FIG. 6D. A stopper portion 13f having a size which can not pass through the through-hole is formed in the middle of the spring 13. After the spring 13 is inserted from the through-hole, a similar stopper portion 13g is formed at the distal end. Between these stopper portions 13f and 13g, urging force is not generated even if the drive shaft 12 rotates because the diameter of the spring 13 does not change until the spring fixing portion 12e moves through the spring 13 and then abuts on one of the stopper portions as indicated by the arrow. The range in which urging force is not generated is the neutral return range.

As described above, according to the present embodiment, it is possible to provide an input unit equipped with the neutral return mechanism having a small-sized, light-weight, and simple configuration and having a sufficient return function.

Fourth Embodiment

Figure 7:
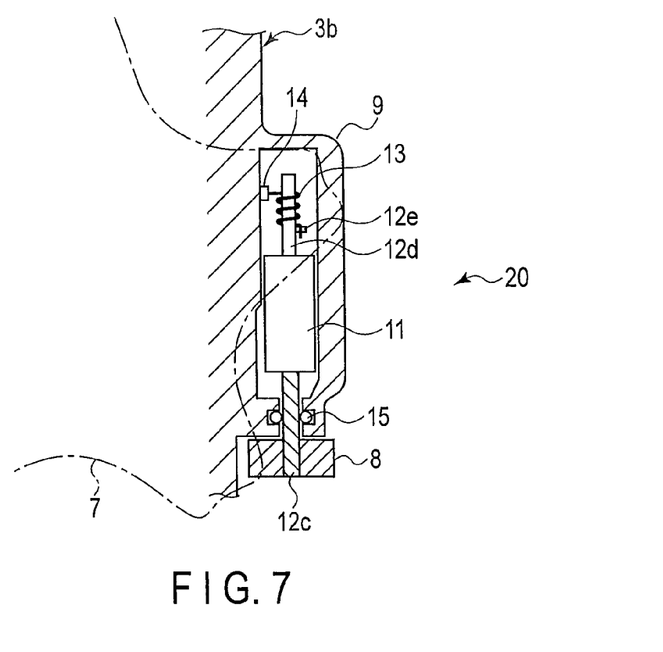
FIG. 7 is a diagram showing the conceptual configuration of an input unit housed in an operation portion according to a fourth embodiment.

FIG. 7 is a diagram showing the conceptual configuration of an input unit housed in an operation portion according to a fourth embodiment. Components in the present embodiment equivalent to those in the first embodiment described above are provided with the same reference signs, and are not described. The input unit according to the present embodiment comprises an operator and a neutral return mechanism. Although not shown, an operation portion 3 according to the present embodiment includes the grip portion 3a and the operation portion body 3b that have been described above. The operation portion body 3b also has a UD knob (rotation knob) 7 and an RL operation dial 8.

An input unit 20 according to the present embodiment comprises an operator and a neutral return mechanism. The operator comprises the RL operation dial 8, a drive shaft 12c erected on the RL operation dial 8, and a double shaft type potentiometer 11 provided at the distal end of a drive shaft 12d. This double shaft type potentiometer 11 is configured so that one shaft passes through the meter main body as a drive shaft. As shown in FIG. 7, one part extending from the meter main body is the drive shaft 12c, and the other opposite part is the drive shaft 12d.

The neutral return mechanism comprises a spring fixing portion 12e provided in the middle of the drive shaft 12d, and a spring 13 (spiral coil spring) fitted to the drive shaft 12d. The spring 13 is fitted to the drive shaft 12d, and has one end fixed to, for example, a rib of the operation portion housing and the other end fixed to the spring fixing portion 12e. The space between the drive shaft 12 and an operation portion housing is watertightly configured by an O-ring 15.

The neutral return mechanism according to the present embodiment is equivalent to that in the third embodiment. When the RL operation dial 8 is rotated, the coil diameter of the spring 13 decreases (decreases in diameter) so that the spring 13 winds around the drive shaft 12, or the coil diameter increases (increases in diameter) so that the spring 13 comes away from the drive shaft 12. As described above, due to the changes in the coil diameter, the RL operation dial 8 is returned to the neutral position by urging force generated in a direction opposite to the direction of the rotational operation.

As described above, according to the present embodiment, it is possible to provide an input unit equipped with the neutral return mechanism having a small-sized, light-weight, and simple configuration and having a sufficient return function. In the present embodiment as well, a proper neutral return range can be set in a configuration shown in FIG. 6D in which a through-hole having a diameter to allow the passage of the spring 13 is made in the spring fixing portion 12e.

Fifth Embodiment

Figure 8:
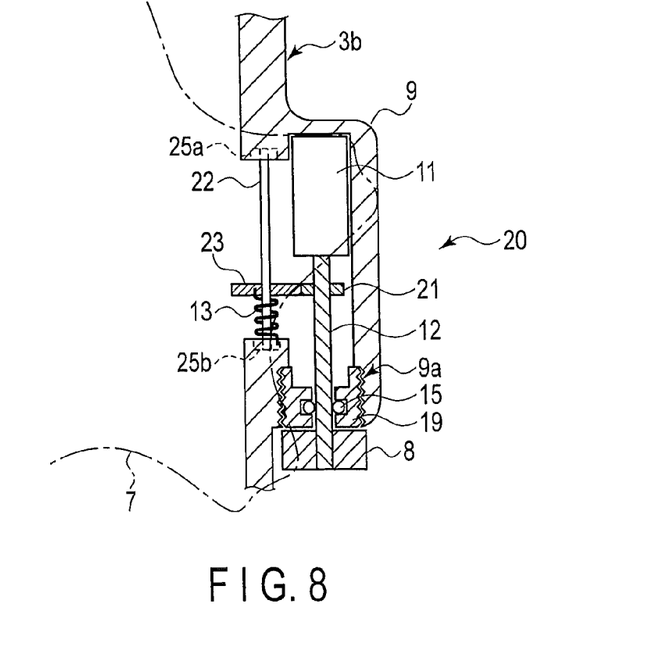
FIG. 8 is a diagram showing the conceptual configuration of an input unit housed in an operation portion according to a fifth embodiment.

FIG. 8 is a diagram showing the conceptual configuration of an input unit housed in an operation portion according to a fifth embodiment. Components in the present embodiment equivalent to those in the first embodiment described above are provided with the same reference signs, and are not described. The input unit according to the present embodiment comprises an operator and a neutral return mechanism. Although not shown, an operation portion 3 according to the present embodiment includes the grip portion 3a and the operation portion body 3b that have been described above. The operation portion body 3b also has a UD knob (rotation knob) 7 and an RL operation dial 8.

An input unit 20 according to the present embodiment comprises an operator and a neutral return mechanism. The operator comprises the RL operation dial 8, a drive shaft 12 erected on the RL operation dial 8, and a potentiometer 11 provided at the distal end of the drive shaft 12. The space between the drive shaft 12 and an operation portion housing is watertightly configured by an O-ring 15.

The neutral return mechanism comprises a gear 21 provided in the middle of the drive shaft 12, a gear 23 which meshes with the gear 21, a coupled driven shaft (potentiometer shaft) 22 which passes through and thus fixes the gear 23, and a spring 13 (spiral coil spring) fitted to the coupled driven shaft 22. Both ends of the driven shaft 22 are smoothly rotatable owing to bearings 25a and 25b. The neutral return mechanism comprises the spring 13 fitted to the coupled driven shaft 22. The spring 13 has one end fixed to the gear 23 and the other end fixed to, for example, a rib of the operation portion housing. The drive shaft 12 and the coupled driven shaft 22 that are coupled by a pair of gears 21 and 23 serving as a transmission mechanism transmit driving force.

In this configuration, the operator rotates the RL operation dial 8. The drive shaft 12 rotates, the rotation is transmitted to the gear 23 from the gear 21 in mesh, and the coupled driven shaft 22 rotates. In response to the rotation of the gear 23, the spring 13 changes so that its coil diameter decreases or increases as shown in FIG. 6B or FIG. 6C. Due to the change in the coil diameter, urging force to return the RL operation dial 8 to the vicinity of the original neutral position works.

As described above, according to the present embodiment, it is possible to obtain advantageous effects equivalent to those in the first embodiment. Moreover, a pair of gears 21 and 23 serving as the transmission mechanism intervene between the drive shaft 12 and the spring 13. Therefore, it is possible to freely set the degree of the urging force of the spring 13 corresponding to the rotation amount of the drive shaft 12 by adjusting a gear ratio.

Sixth Embodiment

Figure 9:
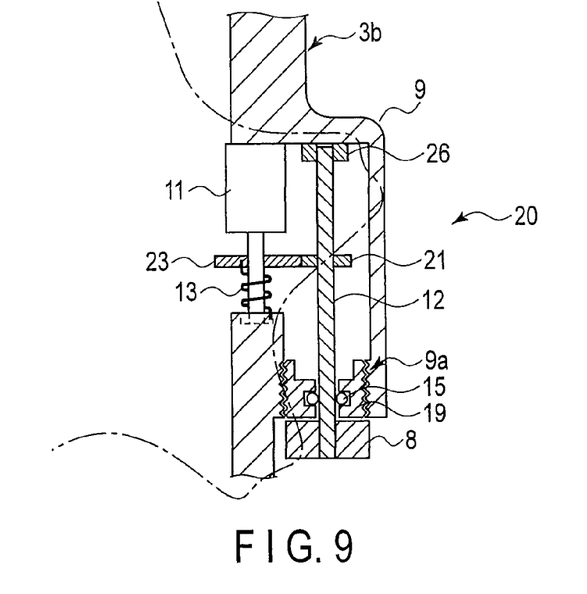
FIG. 9 is a diagram showing the conceptual configuration of an input unit housed in an operation portion according to a sixth embodiment.

FIG. 9 is a diagram showing the conceptual configuration of an input unit housed in an operation portion according to a sixth embodiment. Components in the present embodiment equivalent to those in the first embodiment described above are provided with the same reference signs, and are not described. The input unit according to the present embodiment comprises an operator including a drive mechanism and a potentiometer unit, and a neutral return mechanism. Although not shown, an operation portion 3 according to the present embodiment includes the grip portion 3a and the operation portion body 3b that have been described above. The operation portion body 3b also has a UD knob (rotation knob) 7 and an RL operation dial 8.

The drive mechanism comprises the RL operation dial 8, a drive shaft 12 erected on the RL operation dial 8, a gear 21 provided in the middle of the drive shaft 12, and a bearing 26 provided at the distal end of the drive shaft 12. The potentiometer unit comprises a gear 23 which meshes with the gear 21, and a driven shaft (potentiometer shaft) 22 which passes through and thus fixes the gear 23. The driven shaft 22 has its distal end coupled to an unshown bearing member, and is smoothly rotatable.

The neutral return mechanism comprises a spring 13 (spiral coil spring) fitted to the driven shaft 22. The spring 13 has one end fixed to the gear 23 and the other end fixed to, for example, a rib of the operation portion housing. The drive shaft 12 and the driven shaft 22 that are coupled by a pair of gears 21 and 23 serving as a transmission mechanism transmit driving force.

In this configuration, the operator rotates the RL operation dial 8 to curve a curving potion 4. The drive shaft 12 rotates, the rotation is transmitted to the gear 23 from the gear 21 in mesh, and the driven shaft 22 rotates. In response to the rotation of the gear 23, the spring 13 changes so that its coil diameter decreases or increases as shown in FIG. 6B or FIG. 6C. Due to the change in the coil diameter, urging force to return the RL operation dial 8 to the vicinity of the original neutral position works.

As described above, according to the present embodiment, it is possible to obtain advantageous effects equivalent to those in the first embodiment. Moreover, in the present embodiment, the transmission mechanism comprising the gears 21 and 23 intervene between the RL operation dial 8 and a potentiometer 11. Therefore, it is possible to freely set the rotation amount (rotation angle) of the potentiometer 11 relative to the rotation amount (rotation angle) of the operation dial by setting any gear ratio, and obtain a convenient input unit. For example, if the gear ratio between the gear 21 and the gear 23 is set to 1:3, one rotation of a magnet plate 28 can be set relative to three rotations of the RL operation dial 8.

Seventh Embodiment

Figure 10:
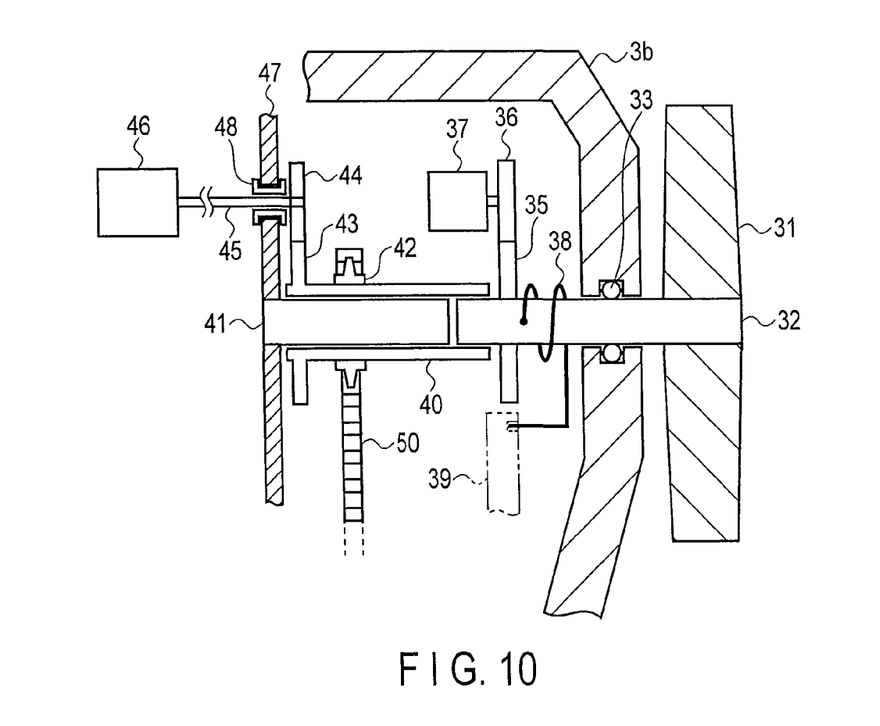
FIG. 10 is a diagram showing the conceptual configuration of an input unit housed in an operation portion according to a seventh embodiment.

FIG. 10 is a diagram showing the conceptual configuration of an input unit housed in an operation portion according to a seventh embodiment. Components in the present embodiment equivalent to those in the first embodiment described above are provided with the same reference signs, and are not described. In the example according to the present embodiment, the input unit is configured so that an operation dial of an operator is applied to the shape of a UD knob 7 shown in FIG. 1.

The input unit comprises an operator and a neutral return mechanism. The operator comprises an operation knob 31, a knob shaft 32 which is fitted in the operation knob 31 and which is inserted in an operation portion 3, a gear 35 fixed to the distal side of the knob shaft 32, a gear 36 which meshes with the gear 35, and a potentiometer 37 having its shaft mounted on the gear 36 and which detects a rotation amount (rotation angle). The space between the knob shaft 32 and an operation portion housing is watertightly configured by an O-ring 33. The neutral return mechanism comprises a spring 38 (spiral coil spring) fitted to the knob shaft 32. The spring 38 has one end fixed to the knob shaft 32 and the other end fixed to, for example, a rib of the operation portion housing.

The distal part of the knob shaft 32 of the operator is rotatably fitted in one end of a circular cylindrical drive member 40 of an electric curving drive mechanism. The electric curving drive mechanism comprises a support shaft 41 erected on a backing plate 47 in the operation portion housing, the circular cylindrical drive member 40 fitted to the support shaft 41, a sprocket 42 provided over the circumference of the circular cylindrical drive member 40, a curving drive gear 43 fixed to the other end of the circular cylindrical drive member 40, a drive gear 44 which meshes with the gear 43, and a motor 46 having a motor shaft 45 fixed to the drive gear 44. A chain 50 is attached to the sprocket 42, and is coupled to a drive member (e.g. a wire or a pulley) of an unshown curving potion to transmit driving force. The knob shaft 32 and the support shaft 41 are separate from each other, and are located close to each other in the circular cylindrical drive member 40. Although a pair of gears 35 and 36 serve as a transmission mechanism by way of example in the present embodiment, the transmission mechanism may comprise two or more gears. It is also possible to set a suitable gear ratio to freely set the rotation amount (rotation angle) of the potentiometer 37 relative to the rotation amount (rotation angle) of the operation knob 31.

In this configuration, the operator rotates the operation knob 31 to curve a curving potion 4. The knob shaft 32 rotates, the rotation is transmitted to the gear 36 from the gear 35 in mesh, and the motor shaft 45 rotates. In response to the rotation of the knob shaft 32, the spring 38 changes so that the coil diameter of the spring 38 decreases or increases as shown in FIG. 6B or FIG. 6C. Due to the change in the coil diameter, urging force to return the operation knob 31 to the vicinity of the original neutral position works.

As described above, according to the present embodiment, it is possible to obtain advantageous effects equivalent to those in the first embodiment. Moreover, the input unit according to the present embodiment is applied to the operation knob 31 that has heretofore been used, and can therefore be easily applied to a manual operation portion currently in the market without size increase. The operation knob according to the present embodiment is applicable to the UD operation knob and the RL operation dial.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An introduction device comprising:
    a curvable curving portion disposed on a distal side of an insertion portion, the curving potion being linear in a neutral state;
    an operation portion disposed on a proximal side of the insertion portion and comprising an electric-driving source to curve the curving potion; and
    an input unit disposed in a housing of the operation portion and inputting a curving instruction to the electric driving source,
    wherein the input unit comprises:
        an operation dial exposed from the operation portion,
        a drive shaft connected to the operation dial and comprising an external-thread screw shaft portion,
        a rotation amount detector fixed to a distal end of the drive shaft,
        a nut portion screwed to the screw shaft portion and movable on the drive shaft upon rotation,
        a guide shaft projecting from the nut portion, and
        a spring portion provided on the guide shaft and generating an urging force in an axial direction of the drive shaft, wherein the input unit changes the urging force which is generated by the spring portion and which linearly works in the axial direction to an urging force in a rotational direction of the nut portion to return the operation dial to the neutral state.

2. The introduction device according to claim 1, wherein the operation dial is provided at a position where fingers of a hand of the operator grasping the operation portion except for the thumb are arranged.

3. The introduction device according to claim 2, wherein the spring portion is located closer to a longitudinal axis of the operation portion than the drive shaft.

4. The introduction device according to claim 2, wherein the operation dial curves the curving portion in a first curving direction; and further comprising an angle knob provided at a position in the operation portion operable by the thumb of the hand of the operator grasping the operation portion, the angle knob being provided rotatably around a rotation axis extending in a direction that intersects with a longitudinal axis of the operation portion, the angle knob curving the curving potion in a second curving direction that intersects with the first curving direction, and the spring portion and the drive shaft are arranged in parallel in a direction along the rotation axis of the angle knob.

5. The introduction device according to claim 1, wherein the spring portion comprises:

a first spring which extends in the proximal direction of the drive shaft and which is fixed to the operation portion, and a second spring which extends in the distal direction of the drive shaft and which is fixed to the operation portion.

6. The introduction device according to claim 5, wherein an urging force causes the nut portion to rotate the drive shaft via the screw shaft portion due to an elastic force which is generated in a rotation axis direction by the first spring or the second spring.

* * * * *